United States Patent
Kleinschmidt et al.

(10) Patent No.: US 6,454,709 B1
(45) Date of Patent: Sep. 24, 2002

(54) TELE-EVALUATION SYSTEM, ESPECIALLY FOR MEDICINE

(76) Inventors: Peter Kleinschmidt, Gebbertstrasse 126, 91052, Erlangen (DE); Klaus Abraham-Fuchs, Graslitzer Strasse 17, 91052, Erlangen (DE)

( * ) Notice: Subject to any disclaimer, the term of this patent is extended or adjusted under 35 U.S.C. 154(b) by 24 days.

(21) Appl. No.: 09/651,578

(22) Filed: Aug. 29, 2000

(51) Int. Cl.[7] .............................................. A61B 5/00
(52) U.S. Cl. ........................... 600/300; 705/3; 128/904
(58) Field of Search .......................... 705/2–4, 22, 28; 600/300–301; 128/903–904, 920–925, 898; 235/454, 462–467

(56) References Cited

U.S. PATENT DOCUMENTS

| | | | | |
|---|---|---|---|---|
| 5,713,350 A | * | 2/1998 | Yokota et al. | 600/300 |
| 6,117,073 A | * | 9/2000 | Jones et al. | 600/300 |
| 6,221,012 B1 | * | 4/2001 | Maschke et al. | 600/301 |
| 6,272,469 B1 | * | 8/2001 | Koritzinsky et al. | 705/2 |

\* cited by examiner

*Primary Examiner*—Kevin Shaver
*Assistant Examiner*—Michael Astorino
(74) *Attorney, Agent, or Firm*—Schiff Hardin & Waite

(57) ABSTRACT

In a tele-evaluation system, especially a tele-medicine system for centralized remote evaluation of information, particularly medical patient information and measurement data, based on one-time use articles (disposable items) that are identified with data and/or can collect measurement data, the disposable items carries an individual encoding key for encoding the data in a patient station that is linked via data line or data network to a storage station and/or evaluation-reception station. A disposable-ID is applied to or stored in the disposable item and is automatically collected at the patient station and is simultaneously transmitted unencoded, with an identifier for the patient station. The reception station has a data link to the disposable item manufacturer in order to query, using the disposable-ID, the individual key for decoding the data.

12 Claims, 2 Drawing Sheets

TELE-EVALUATION SYSTEM, ESPECIALLY FOR MEDICINE

BACKGROUND OF THE INVENTION

1. Field of the Invention

The present invention applies to a tele-evaluation system, particularly for the centralized remote evaluation of information, particularly medical patient information and measurement data, based on one-time use articles (disposables) that are characterized with data and/or can gather measurement data.

2. Description of the Prior Art

Problems and new opportunities arise for tele-medical treatment management and treatment monitoring via networks, such as for medical purposes, but also for non-medical purposes. A significant problem in such networks is data security. The danger exists that the treatment data may be read by persons gaining unauthorized access to the network which, at a minimum, is an invasion of the privacy of a patient. The consequences can be even worse if the diagnosis data and treatment data are deliberately changed by persons with criminal intent. The risk of accidental mismatching of physician and patient addresses also must be reduced in such a tele-medical treatment management. If these problems are adequately revised, a tele-medical treatment management provides the possibility of acquiring reliable evidence about the effect of methods and medicine prescriptions as a result of the centralized collection of the treatment data. Moreover, a geographical spread of illnesses can be more quickly recognized by means of a tele-medical treatment management.

It is obvious to encode the data during transmission, but the problem is that many codes can be very easily cracked. There are indeed numerous suggestions of how secure keys (e.g. 128 bit) can be used and how these can be administered, in an expeditious manner, in security centers that also guarantee the authenticity of the sender. Additionally, solutions are known in banking systems, wherein the authentication is realized by the forwarding of registered transaction numbers, which must be processed in sequence. Common factors for all of these proposals are that they are expensive and inconvenient for those involved.

SUMMARY OF THE INVENTION

An object of the present invention is to provide a tele-evaluation system of the type initially described wherein secure data transmission from the patient or the physician to an evaluation station is possible without using long complicated keys and wherein a number of uses of the collected patient data is possible.

This object is inventively achieved in a tele-evaluation system wherein disposable items used in the system to collect data carry an individual encoding key in order to encode the data in a patient station that is connected via a data line or a data network to a storage station and/or evaluation reception station. A disposable-ID, that is introduced into or stored on the disposable item and can be automatically collected (entered) at the patient station, is simultaneously transmitted unencoded together with the encoded data and an identifier for the patient station. The reception station has a data link to the manufacturer of the disposable item in order to query the individual key via the disposable-ID for decoding of the data.

The patient station thus can be located at the patient's home, at the physician's office, in a clinic, at an ambulatory care service, at an emergency facility or at any other location, at which the patient uses it. The manufacturer of the disposable items (or alternatively an authorized distributor of the disposable items)—announces the individual encoding keys of each disposable item (that can be identified by its disposable ID) via a secure (certified) data line to the evaluation station, so that this key can decode the data transmitted by the patient station using the individual keys and can continue processing.

This further processing can transpire, for example, by the evaluation-reception station sending back diagnoses or such to the patient station via the data line or the data network, using the respectively changing individual keys of the disposable item after evaluating the disposable item data.

The key can be kept much shorter and simpler because the encoding of the patient data (acquired via a disposable item) ensues with an individual key that is allocated only to this one disposable item, i.e. by dispensing with the use of a key with which all data are to be transmitted, so that the application is much simpler and less expensive. Given 128 bit keys, the keys in many instances in conventional systems are considerably longer than the actual information to be encoded.

Via the disposable-ID and the accompanying identifier of the patient station, i.e. the identifier for the attending physician, clinic or such, the information can be securely sent back to the patient station, where a decoding is possible in turn using the individual keys (of the disposable items) available there. Therefore, a very secure data transmittal is achieved without, complicated keys and without the necessity of using a secured data line.

The evaluation-reception station can be connected in an embodiment of the invention to the disposable-ID storage of the disposable item manufacturer via a secure data line, which makes only one or a few secure data lines from the one or the few evaluation-reception stations necessary. In contrast thereto, there are thousands of patient stations, from which secure data lines to the evaluation stations are, as a practical matter, not realizable.

In a further embodiment of the invention, the reception station is linked to a central patient data bank and/or to an expert system for evaluating the data on the basis of the stored technical knowledge for issuing an individual diagnosis.

The inventive tele-evaluation system also enables linking the reception station to an accounting computer that individually calculates the fee for the service rendered on the basis of the disposable-ID and the identifier of the patient station.

Moreover, the inventive tele-evaluation system also allows the implementation of a security system wherein the reception station is provided with a storage-blocking step that blocks information from a one-time-use disposable item for which the ID has already been logged in once before in a data input and/or issues a notice to a surveillance site. In this manner, disposable items intended and designed only for a one-time use cannot be re-used by the patient or physician in an unallowable fashion endangering the patient and the accuracy of the data ascertained.

In a further embodiment of the invention, the reception station, upon querying the individual key, simultaneously receives information concerning the calibration factors of disposable measurement devices and/or efficacy factors and/or the manufacturing data of medicines. Thus, for example, a complicated equalization of measurement chips with different calibration factors is not required at the manufacturer of the disposable item, but rather it suffices that the calibration curves are stored at the manufacturer and are allocated to the individual disposable item so that they are transmitted upon querying the individual key and can be correspondingly considered during the evaluation.

In another embodiment of the invention, the reception station is a neutral, manufacturer-independent health center that uses a disposable item to forward the patient data concerning success, compatibility, side effects or such of a treatment to the patient station, as well as anonymously to the disposable item manufacturer. This enables the acquisition of reliable findings concerning the effect of methods and medicine prescriptions with simultaneous assurance of the necessary anonymity of the patients.

An example of a disposable item, i.e. a one-time use item that is suitable for an inventive tele-evaluation system, is a diagnostic bio-chip, e.g. a sensor chip, that can acquire and evaluate a number of blood factors by analyzing blood taken from a patient.

Another example is medicine and/or its individual packaging, for example, by encoding each tablet individually or using an individual code for the packaging (bottle, tube, packet, etc.) a verification can take place whether it is the correct tablet, whether the correct number have been taken, etc. Also, specimen-taking utensils for blood, urine, breath, i.e. items referred to as hygiene items, can represent disposable items (that can be more readily evaluated with the aid of the inventive tele-evaluation system). These include, inter alia, measurement electrodes, diagnosis measurement strips, hygiene overlays (examination table, paper, gloves, etc.) for measurement and training devices as well as lists or simulators, using transaction numbers and key codes.

Examples for the introduction and readout of encoding data for placing the disposable-ID on the respective disposable item are optically visible patterns, such as alphanumerics or symbols, that are legible by humans and can be transcribed, e.g. via a keyboard, electric contact patterns that can be electrically picked up, chips that can be read out, a bar code that can be optically decoded (possibly including color) with a pen, scanner or image processor as well as high-frequency resonators that can be read out radio transmission, magnetic strips that can be read out with customary card readers biochemical, electrical or fluorescent markers that can be optically read out, etc.

DESCRIPTION OF THE PREFERRED EMBODIMENTS

Figure 1:
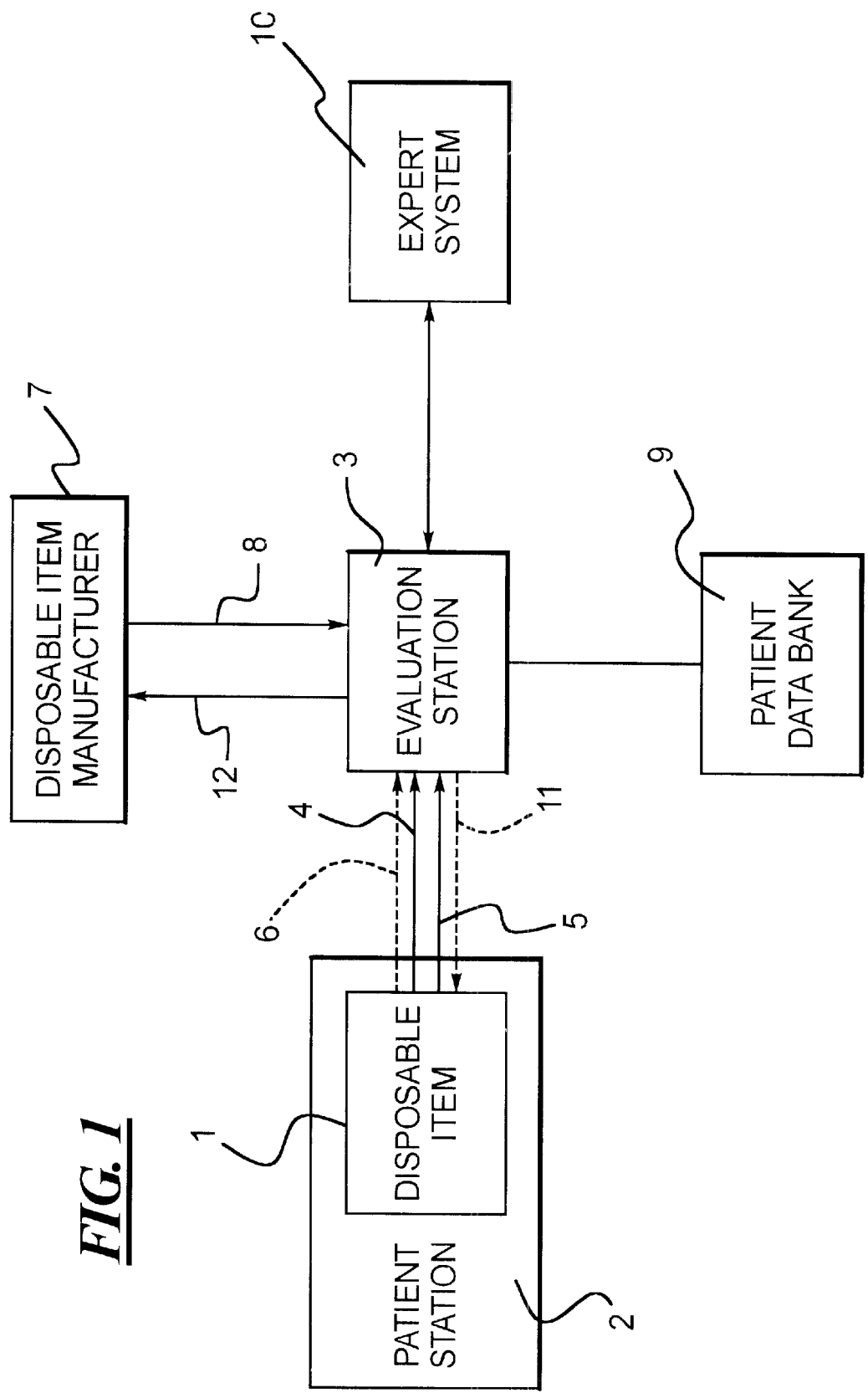
FIG. 1 is a schematic block diagram of the partially encoded and unencoded information transmission between the basic stations of an inventive tele-evaluation system.

The acquired patient information from the patient station 2, i.e. from a sending station at the patient's home, at the physician's office, in a clinic, at an ambulatory care service, at an emergency facility or such, is encoded via an individual key (allocated only to the respective disposable item) is sent by the patient station 2 to the evaluation station 3. The disposable item 1 in FIG. 1, is a diagnostic bio-chip, for example. At the same time as the encoded disposable data are transmitted, the disposable-ID 5 (unencoded) for identifying the disposable item 1 from which the information has been acquired, is also transmitted and furthermore, if warranted, a transmittal of the identifier 6 of the patient station 2 simultaneously occurs. The evaluation station 3 is, e.g. linked to the disposable item manufacturer 7 via a secure data line and receives therefrom the individual key allocated to this disposable item 1 as information 8 upon giving the disposable-ID 5. With this individual key, the evaluation station 3 can decode the disposable data 4 and evaluate it using, as needed, a central patient data bank 9 and an expert system 10 and can issue a corresponding diagnosis. This can then be returned to the patient station 2 as data information encoded, in turn, with the same individual key, where it can be decoded using the present key of the disposable item 1 and also allocated again to the respective patient. The data concerning the patient does not need to be delivered in tandem to the evaluation station 3, unless of course, the patient or physician would like to makes use of the central patient data bank 9. In this case, the patient information can be given either unencoded—due to the encoding of the other essential data, this is not security-related—or the patient data can be encoded with the same individual disposable-key.

The inventive tele-medicine system schematically shown in FIG. 1 enables another especially meaningful and significant evaluation of many patient datasets that have been collected by allowing them to be anonymously forwarded to the respective disposable item manufacturer as data 12 from the evaluation system 3. For this purpose, the evaluation-reception station 3 is linked with a number of disposable item manufacturers. Each disposable item manufacturer receives only anonymous patient data concerning the success, compatibility, side effects or such of a treatment which occur using a disposable item from that manufacturer.

Figure 2:
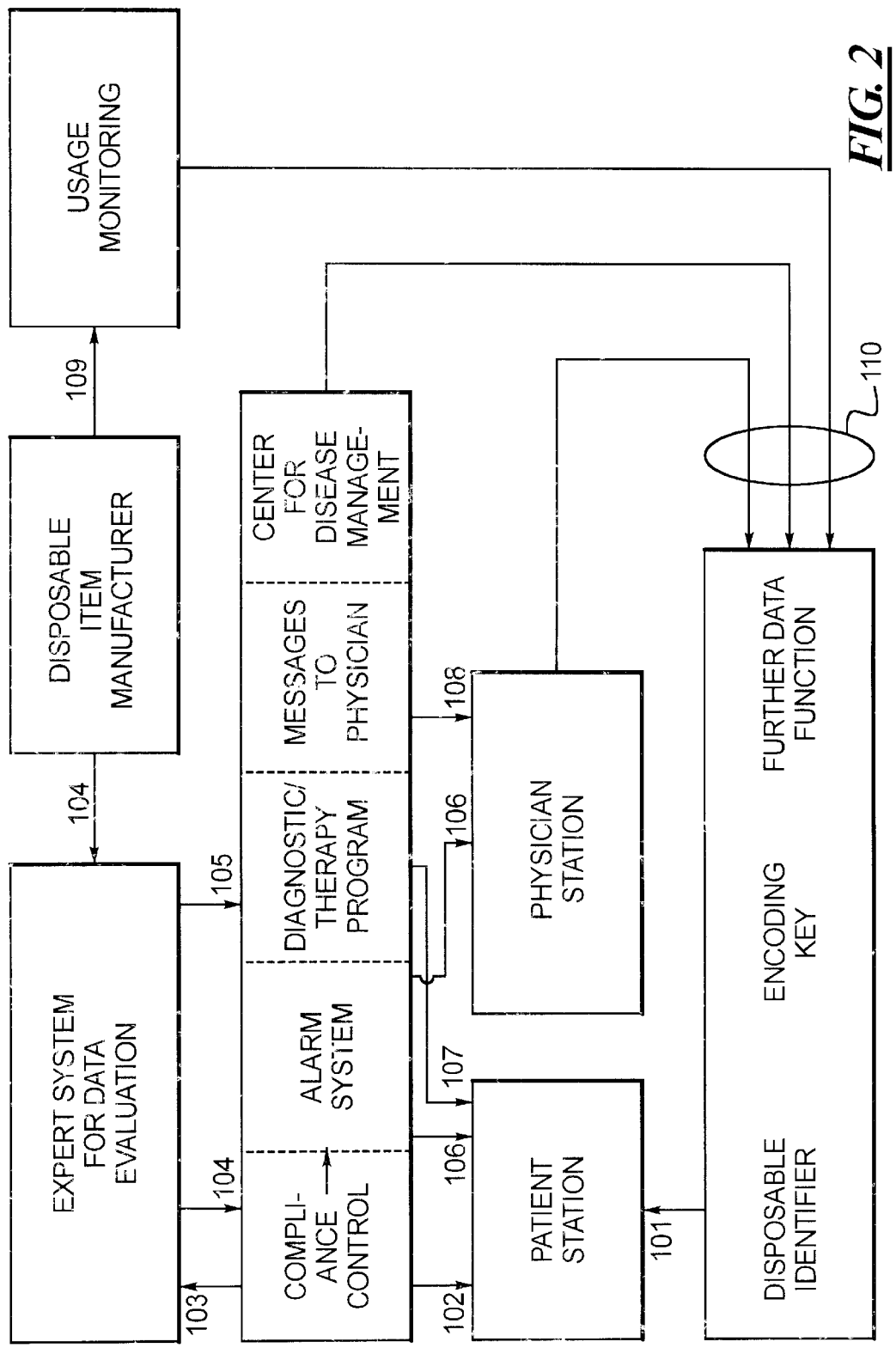
FIG. 2 is a schematic layout of an expanded inventive tele-medical disease management system.

FIG. 2 schematically shows a tele-medical disease management system, in the varied, additional evaluation possibilities of the patient information already described above can be utilized in a comprehensive manner.

The reference characters in FIG. 2 respectively signify the following:

identifies the data transfer from the disposable item, the secure transmittal of the data encoded using a one-time code, the transmittal of the diagnosis/therapy results data for the central expert system, the sending of the list with the disposable-ID/key/disposable-info (medicine info), diagnostic factors to be transmitted back, patient information given irregularities, progress-dependent patient information and care using new or adapted care/therapy phases, regular information for the attending physician concerning condition and progress, putting the disposable items to use, recommendation based on usage, and function of the disposables.

The function of disposables means, for example, a medicine, a hygiene item for trainers or a measurement device, measurement electrodes, test strips, one-time-use sensors, a specimen-taking device or such.

The invention is not limited to the exemplary embodiments shown, so that it would even be possible to also implement, in particular, an accounting system in the inventive tele-medicine system or storage blocking steps that prevent a multiple use of a disposable item.

Although modifications and changes may be suggested by those skilled in the is the intention of the inventors to embody within the patent warranted hereon all changes and modifications as reasonably and properly come within the scope of their contribution to the art.

We claim as our invention:

1. A tele-evaluation system for centralized remote evaluation of medical patient information and medical measurement data comprising:

a plurality of one-time usable; disposable items associated with a medical procedure having data associated therewith;

each disposable item having a unique disposable identifier associated therewith and each disposable item also carrying a unique encoding key for encoding said data associated with the medical procedure for which the disposable item is employed;

a patient station and an evaluation station located remote from said patient station, said patient station and said evaluation station being in data communication via a data link selected from the group consisting of a data line and a data network;

said patient station having a data interface via which said data associated with said medical procedure are entered into said patient station in encoded form, according to said encoding key carried by the disposable item employed in the medical procedure;

said patient station transmitting, to said evaluation station said data in encoded form, and said disposable identifier with no encoding, together with an identifier for a patient who participated in the medical procedure, and said evaluation station being connected via a data link to a manufacturer of said disposable item to transmit said disposable identifier to said manufacturer to obtain, in return, said encoding key, via said disposable identifier, for decoding said data; and said evaluation station evaluating said data to produce diagnostic information and transmitting said diagnostic information back to said patient station via said data link.

2. A tele-evaluation system as claimed in claim 1 wherein said disposable identifier is represented by readable information applied to said disposable item.

3. A tele-evaluation system as claimed in claim 1 wherein said disposable identifier is electronically stored in a chip in said disposable item.

4. A tele-evaluation system as claimed in claim 1 wherein said evaluation station transmits diagnostic information via said data link back to said patient station after evaluating said data associated with said medical procedure.

5. A tele-evaluation system as claimed in claim 1 wherein said data link between said evaluation station and said manufacturer is a secure data line.

6. A tele-evaluation system as claimed in claim 1 wherein, upon transmittal of said disposable identifier from said reception station to said manufacturer, said manufacturer, in addition to said encoding key, transmits information selected from the group consisting of calibration factors for a measurement device employing said disposable item, efficacy factors related to a measurement device employing said disposable item, and information relating to medicine for said medical procedure back to said evaluation station.

7. A tele-evaluation system as claimed in claim 1 further comprising a central patient data bank having a communication link to said evaluation station.

8. A tele-evaluation system as claimed in claim 1 wherein said evaluation station has access to an expert system for evaluating said data.

9. A tele-evaluation system as claimed in claim 1 further comprising an accounting computer, having a communication link with said evaluation station which individually calculates a fee for a service associated with use of said disposable item identified by said disposable identifier.

10. A tele-evaluation system as claimed in claim 1 wherein said evaluation station includes means for blocking receipt, from said patient station, of a disposable identifier that has been previously received at said evaluation station.

11. A tele-evaluation system as claimed in claim 1 wherein said evaluation station, in addition to said diagnostic information, transmits back to said patient station information relating to said medical procedure selected from the group consisting of success rates, compatibility information and side effects, and also anonymously transmits information to said manufacturer via said data link regarding usage of said disposable item.

12. A method for tele-evaluation of medical information comprising the steps of:

providing a plurality of one-time usable, disposable items respectively for use in medical procedures having data associated therewith;

uniquely identifying each of said disposable items with a disposable identifier and permanently associating each disposable item with an individual encoding key;

at patient station, entering said data associated with said medical procedure together with information about a patient who participated in the medical procedure, together with said disposable item identifier and said encoding key;

establishing a communication link between said patient station and an evaluation station remote from said patient station;

via said communication link, transmitting said data associated with said medical procedure, said patient information and said disposable identifier to said evaluation station with at least said data associated with the medical procedure being encoded using said encoding key, and with said disposable identifier being transmitted unencoded;

upon receipt of the encoded data associated with the medical procedure, and the disposable ID, at the evaluation station, said evaluation station establishing a further communication link with a manufacturer of said disposable item;

via said further communication link, said evaluation station transmitting said disposable identifier to said manufacturer and in return obtaining said encoding key from said manufacturer, and, at said evaluation station, decoding said data associated with said medical procedure to obtain decoded data; and at said evaluation station, evaluating said decoded data to obtain diagnostic information and transmitting said diagnostic information back to said patient station via said communication link.

\* \* \* \* \*